United States Patent [19]

Schleger et al.

[11] Patent Number: 5,633,692

[45] Date of Patent: May 27, 1997

[54] FACIAL PROTECTIVE WEAR, PARTICULARLY FOR PROTECTION FROM THE SUN

[75] Inventors: Linda Schleger, deceased, late of Elmhurst, N.Y., by Stanley Schleger, legal representative; Thomas Yang, Elmhurst, N.Y.; Adam Kaufer, Rockville Center, N.Y.

[73] Assignee: The Estate of Linda Schleger, Kings Point, N.Y.

[21] Appl. No.: 379,887

[22] Filed: Jan. 27, 1995

[51] Int. Cl.⁶ ............................ G02C 7/10; G02C 5/08
[52] U.S. Cl. ........................ 351/44; 351/41; 351/63; 2/454
[58] Field of Search ........................... 351/63, 136, 137, 351/138, 139, 41, 44, 65, 78, 79, 80, 81, 88, 131, 132, 158; 2/454, 445, 426, 436, 437, 12, 13

[56] References Cited

U.S. PATENT DOCUMENTS

| | | |
|---|---|---|
| 274,385 | 6/1883 | Newcomb. |
| D. 294,952 | 3/1988 | Wilson ............................. D16/110 |
| D. 314,001 | 1/1991 | Nussbicki ........................ D16/102 |
| D. 314,391 | 2/1991 | Nussbicki ........................ D16/102 |
| D. 321,703 | 11/1991 | Grau ................................. D16/112 |
| D. 322,616 | 12/1991 | Wiedner .......................... D16/102 |
| 1,799,064 | 3/1931 | Rickerd. |
| 2,026,741 | 1/1936 | Kintz. |
| 2,037,772 | 4/1936 | Everett et al. .................... 351/41 |

(List continued on next page.)

FOREIGN PATENT DOCUMENTS

| | | |
|---|---|---|
| 0293593 | 7/1988 | European Pat. Off.. |
| 721069 | 2/1932 | France. |

*Primary Examiner*—Hung X. Dang
*Attorney, Agent, or Firm*—Ostrolenk, Faber, Gerb & Soffen, LLP

[57] ABSTRACT

Facial protective wear comprising a lens portion for disposition over each eye of a wearer, a support frame for attaching each lens portion thereto, temple bars coupled hingedly to respective outwardly extending portions of the frame, the temple bars being adapted to provide support on the wearer's ears and a nose support disposed between the lens portions for supporting the facial protective wear on the wearer's nose. Preferably a nose protective portion is disposed between the lens portions. The nose protective portion can take a variety of forms. The frame may be divided into two frame portions, the two frame portions each supporting a respective lens portion, the two frame portions being hingedly coupled together between the two lens portions at, for example, the nose protective portion, so that the facial protective wear can be collapsed for storage.

38 Claims, 11 Drawing Sheet

U.S. PATENT DOCUMENTS

| | | | |
|---|---|---|---|
| 2,191,937 | 2/1940 | Low . | |
| 2,384,405 | 9/1945 | Crowther . | |
| 2,395,297 | 2/1946 | Shock . | |
| 2,519,561 | 8/1950 | Gillman et al. . | |
| 2,537,248 | 1/1951 | Vigano | 351/63 |
| 2,669,717 | 2/1954 | Diggs . | |
| 3,155,982 | 11/1964 | Baratelli | 2/12 |
| 3,233,249 | 2/1966 | Baratelli et al. | 2/14 |
| 3,233,250 | 2/1966 | Jonassen | 2/14 |
| 3,298,031 | 1/1967 | Morgan . | |
| 3,383,707 | 5/1968 | McNeill | 2/12 |
| 3,384,903 | 5/1968 | Malcom, Jr. | 2/14 |
| 3,678,929 | 7/1972 | Buscher . | |
| 3,705,760 | 12/1972 | Langendorfer et al. . | |
| 4,101,930 | 7/1978 | Sanders et al. | 358/183 |
| 4,101,980 | 7/1978 | Stepan et al. | 2/9 |
| 4,271,538 | 6/1981 | Montesi et al. | 2/439 |
| 4,507,809 | 4/1985 | Stepan | 2/424 |
| 4,515,448 | 5/1985 | Tackles . | |
| 4,527,291 | 7/1985 | Nussbicki | 2/450 |
| 4,541,125 | 9/1985 | Phillips . | |
| 4,621,378 | 11/1986 | Hatchman . | |
| 4,649,577 | 3/1987 | Wiedner | 2/436 |
| 4,674,851 | 6/1987 | Jannard | 351/47 |
| 4,730,915 | 3/1988 | Jannard | 351/47 |
| 4,741,611 | 5/1988 | Burns | 351/4 |
| 4,786,159 | 11/1988 | Piazza, Sr. et al. . | |
| 4,835,796 | 6/1989 | Wiedner | 2/431 |
| 4,843,655 | 7/1989 | Hegendörfer | 2/449 |
| 4,859,048 | 8/1989 | Jannard | 351/159 |
| 4,867,550 | 9/1989 | Jannard | 351/47 |
| 4,868,930 | 9/1989 | Blackstone | 2/439 |
| 4,877,320 | 10/1989 | Holden | 351/44 |
| 4,944,039 | 7/1990 | Dietrich . | |
| 4,951,322 | 8/1990 | Lin | 2/439 |
| 4,976,530 | 12/1990 | Mackay et al. | 351/44 |
| 4,991,952 | 2/1991 | Grau | 331/120 |
| 5,012,527 | 5/1991 | Michel . | |
| 5,220,689 | 6/1993 | Miller | 2/12 |
| 5,225,857 | 7/1993 | Sakamoto | 351/63 |
| 5,379,463 | 1/1995 | Schleger et al. | 2/431 |
| 5,379,464 | 1/1995 | Schleger et al. | 2/431 |

FACIAL PROTECTIVE WEAR, PARTICULARLY FOR PROTECTION FROM THE SUN

BACKGROUND OF THE INVENTION

The present invention relates to facial protective wear, and particularly, facial wear for protecting the eyes and upper cheeks and nose from damaging radiation from the sun. The invention also has applications as facial wear for protection from the wind and also from flying objects, i.e., but is particularly applicable as facial wear for protection from solar rays. The present invention provides the function available from what is commonly known as sunglasses, but also fulfills additional facial protective functions such as protecting the very sensitive and easily sunburned areas of the upper face, such as the nose and upper cheeks. The present invention is useful particularly in situations where there is substantial risk of overexposure to the sun's rays, and thus is useful in preventing sunburns and skin cancers caused by such overexposure.

Various forms of sunglasses and protective eyewear have been developed in the past. Applicant is aware of the following patents relating to sunglasses and protective eyewear:

U.S. Pat. Nos. 4,271,538; 4,976,530; 4,835,796; 4,507,809; 4,649,577; 4,991,952; 4,843,655; 4,527,291; Des. 314,391; Des. 294,952; Des. 314,001; Des. 321,703; Des. 322,616; 3,155,982; 3,233,249; 3,233,250; 3,384,903; 4,674,851; 4,730,915; 4,741,611; 4,824,233; 4,859,048; 4,867,550; 4,877,320; 4,951,322; 4,101,930; 4,101,980; 4,621,378; 4,868,930; 3,383,707; 5,220,689; 3,705,760; 2,385,405; 2,395,297; 2,669,717; 4,541,125; 4,944,039; 5,012,527; 3,298,031; 1,799,064; 2,191,937; 4,515,448; 2,456,334; 5,182,586; EP 334701; FR 1,488,442; U.S. Pat. Nos. 4,786,159; 4,527,291; 3,705,760; 2,037,772; 274,385;

SUMMARY OF THE INVENTION

It is an object of the present invention to provide facial protective wear, e.g., eyewear.

It is yet still a further object of the invention to provide facial wear which protects a wearer from solar rays and/or which attenuates the intensity of solar radiation.

It is a further object of the invention to provide a functional and acceptable cosmetic device for the protection of the central facial area against ultraviolet light (30% of all skin cancers occur on the nose and 8% around the eyes).

Ultraviolet light (UV) is a known cause of skin cancer as well as premature aging of the skin (i.e. wrinkles, dark spots, rough spots, broken blood vessels). The UVB spectrum (290–320) nanometers) causes the most change with a lesser contribution from the UVA range (320–400 nanometers).

There appears to be a relationship between UV light and eye cataract formation and other chronic eye conditions (up to 520 nanometers-blue light).

Accordingly, it is a further object of the invention to provide protection against UVB (290–320 nanometers) and protection against UVA (320–400 nanometers).

It is yet still a further object of the present invention to provide facial wear which protects not only the wearer's eyes, but other facial features, including the nose, upper cheeks and temples, and which prevents damaging radiation from reaching the wearer's eyes and other facial features both directly and also preferably from the side of the head.

It is yet still a further object of the present invention to provide facial wear for protecting a wearer's face from windburn and from damaging flying objects.

It is yet still a further object of the present invention to provide facial protective wear for protecting the wearer's eyes as well as the wearer's nose from the harmful effects of solar radiation.

In particular, it is an object of the present invention to provide such eye and nose area protection in a fashionable manner.

According to one embodiment, it is an object of the present invention to provide facial protective wear including a nose protective portion which provides adequate ventilation to the wearer's nose and eye areas while still protecting against harmful solar radiation.

It is a further object of the present invention to provide facial protective wear that is collapsible into a small size for storage.

The above and other objects of the present invention are achieved by facial protective wear comprising: a lens portion for disposition over each eye of a wearer; a support frame for attaching each lens portion thereto; temple bars coupled hingedly to respective outwardly extending portions of the frame, the temple bars being adapted to provide support on the wearer's ears; a nose support disposed between the lens portions for supporting the facial protective wear on the wearer's nose; and a nose protective portion disposed between the lens portions, the nose protective portion comprising a plurality of horizontally disposed louvers arranged between the lenses.

Preferably, the lens portions substantially prevent passage of damaging ultraviolet radiation (UVA/UVB) and also lower the intensity of solar radiation reaching the eyes and face.

The above and other objects of the invention are also achieved by facial protective wear comprising: a lens portion for disposition over each eye of a wearer; a support frame for attaching each lens portion thereto; temple bars coupled hingedly to respective outwardly extending portions of the frame, the temple bars being adapted to provide support on the wearer's ears; a nose support disposed between the lens portion for supporting the facial protective wear on the wearer's nose; a nose protective portion disposed between the lens portions; and the frame being divided into two frame portions, the two frame portions each supporting a respective lens portion, the two frame portions being coupled together with a hinge between the two lens portions at the nose protective portion so that the facial protective wear can be folded into a collapsed state for storage.

The above and other objects of the invention are also achieved by facial protective wear comprising: a lens portion for disposition over each eye of a wearer; a support frame for attaching each lens portion thereto; temple bars coupled hingedly to respective outwardly extending portions of the frame, the temple bars being adapted to provide support on the wearer's ears; a nose support disposed between the lens portions for supporting the facial protective wear on the wearer's nose; and the frame being divided into two frame portions, the two frame portions being hingedly coupled together at a location between the two lens portions, the two frame portions being of unequal length, whereby one frame portion is a longer frame portion and the other is a shorter frame portion, the shorter frame portion and its associated temple bar nesting in the longer frame portion and its associated temple bar when the facial protective wear is collapsed for storage.

Other objects, features and advantages of the present invention will become apparent from the following description of the invention which refers to the accompanying drawings.

BRIEF DESCRIPTION OF THE DRAWINGS

The invention will described in greater detail in the following detailed description with reference to the drawings in which.

DETAILED DESCRIPTION OF THE INVENTION

With reference now to the drawings, various embodiments of facial wear according to the invention are shown. With reference to the different embodiments, like reference numerals or like reference numerals with prime designations will be used for like components even though the shape or configuration of the component may be changed in the different embodiments.

With reference to a first embodiment shown in FIGS. 1 through 5, the facial wear according to the invention includes two lens portions 10, one for each of the wearer's eyes. Each lens may be formed of a suitable plastic material, for example, polycarbonate. Glass could also be used, but plastic is preferable for its light weight. The transparent lens portions 10 allow visible light to pass to the wearers's eyes and face, but substantially prevent damaging ultraviolet radiation from reaching the wearer's eyes and face, as well as substantially attenuating solar radiation passing to the wearer's face. The lens portions 10 may thus be suitably tinted or colored and may be made large enough, as shown in the various embodiments herein, and as suitably modified by those of skill in the art appreciating this specification, to cover substantial portions of the wearer's cheeks and side temple portions of the head.

Figure 1:
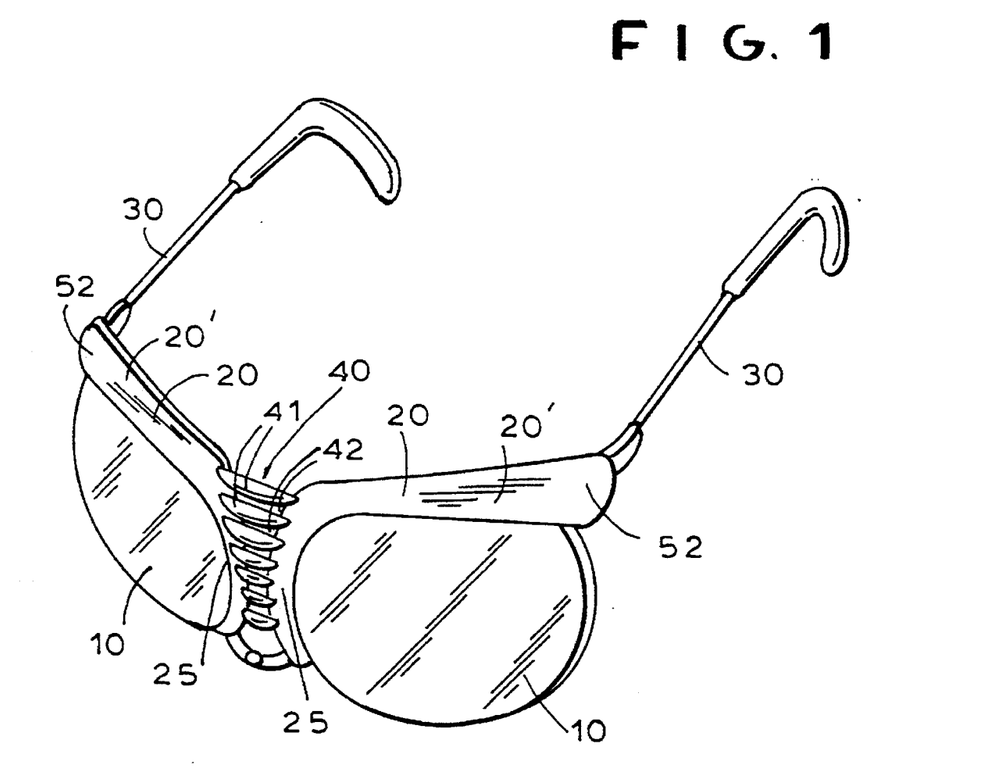
FIG. 1 is a perspective view of a first embodiment of facial wear according to the present invention.

The embodiment shown in FIG. 1 includes a frame 20. The frame 20 at extremities 52 thereof is hingedly coupled to temple bars 30 which allow the facial wear to be supported on the wearer's ears. In addition, the frame 20 includes a downwardly directed connecting nose protective portion, generally designated 40, which is disposed between each of the lens portions 10. In the embodiment shown, the connecting portion 40 is constructed of a series of horizontal louvers 41, each connected to downwardly depending portions 25 of the frame 20. The louvers 41 are slanted downwardly, to prevent solar radiation which is transmitted substantially from above, from reaching the wearer's nose. The areas 42 between the louvers are open, to allow ventilating air to reach under the facial wear and cool the wearer's eyes and nose. Due to the angle of the louvers 41, as shown in cross section in FIG. 5, the open areas 42 are in the shadow of the louvers, thus preventing solar radiation from impinging on the wearer's nose. The connecting portion 40 is made substantially large and extends downwardly sufficiently so that a substantial portion of the wearer's nose is covered by the connecting portion. The connecting portion 40 may be large enough to cover substantially the wearer's entire nose. The connecting portion preferably includes one louver 41 which is coupled to a nose piece 43, shaped to comfortably rest on the wearer's nose and made of a material which provides comfort. Other methods of providing a nose support, as will be apparent to those of skill in the art, may also be employed.

Figure 2:
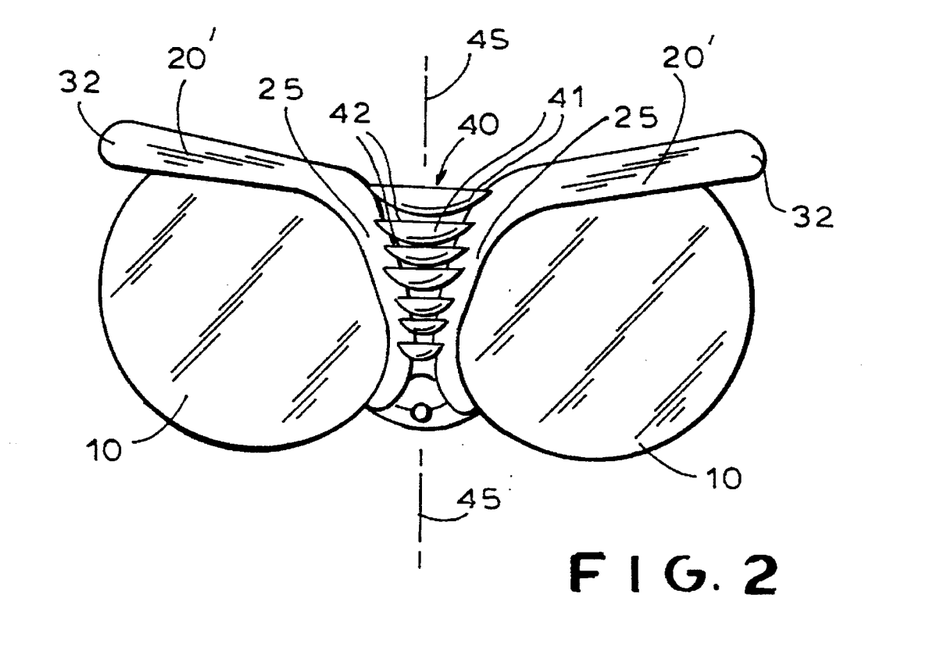
FIG. 2 is a front view of facial wear according to FIG. 1.
Figure 3:
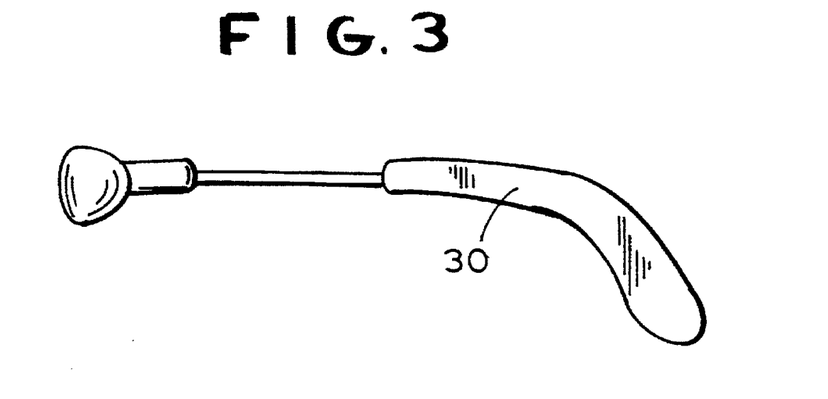
FIG. 3 is a side view of a temple bar of the facial wear of FIG. 1.
Figure 4:
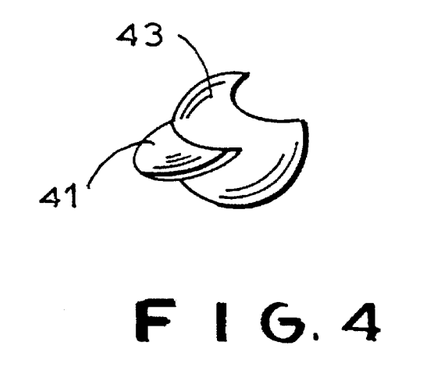
FIG. 4 a perspective view of a portion of the facial wear of FIG. 1, and in particular, the nose piece support.
Figure 5:
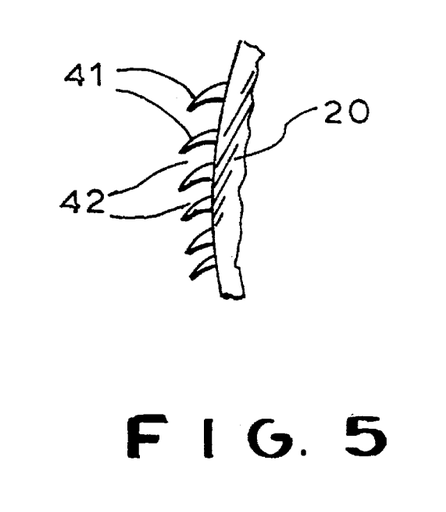
FIG. 5 is a side view of a portion of the facial wear according to FIG. 1, taken through the nose protective member.

The facial wear according to the present invention thus has a nose protective portion 40 which is provided between the lens portions 10. The nose protective portion 40 comprises the downwardly depending sections 25 of the frame 20 and a plurality of louvers 41 as shown in FIGS. 1 and 2. The louvers are angled downwardly to provide protection from the sun, as shown in FIG. 5. The louvers and frame portion 20 may be made of any suitable material, for example, plastic or metal.

Temple bars 30 are attached at ends 52 of the frame portion 20 by suitable known means, for example, hinges.

The embodiment of the facial wear shown in FIGS. 1-5 provides protection for the wearer's eyes and upper check portions by the lens portions 10, and the nose protective portion 40 protects the nose from the harmful effects of the sun, substantially shielding the wearer's nose from the sun.

For convenient storage, the embodiment of FIGS. 1-5 can also be made so that a hinge is provided through the nose protective portion 40, with the frame thus being divided into two approximate half portions 20', as shown in the embodiment of FIGS. 6-9. The two frame portions 20' can hinge at the approximate center line 45 of the nose protective portion, as shown in FIG. 2. The louvers 41, in such an embodiment, may be connected only to one downwardly depending portion 25 of the frame portions 20', so that when the facial wear is collapsed into its folded state, as shown in detail in the other embodiments described, the louvers remain connected to only one of the frame portions 20'. Alternatively, the louvers can be interleaved so that louvers 41 are alternately connected to one portion 25 or the other portion 25. Still according to another variation, the louvers 41 may be split in the middle along the hinge line 45.

Furthermore, although in FIG. 1 the lens portions 10 are not shown with a frame extending completely around their circumference, such a full perimeter frame could also be employed, as will be appreciated by those of skill in the art.

Figure 6:
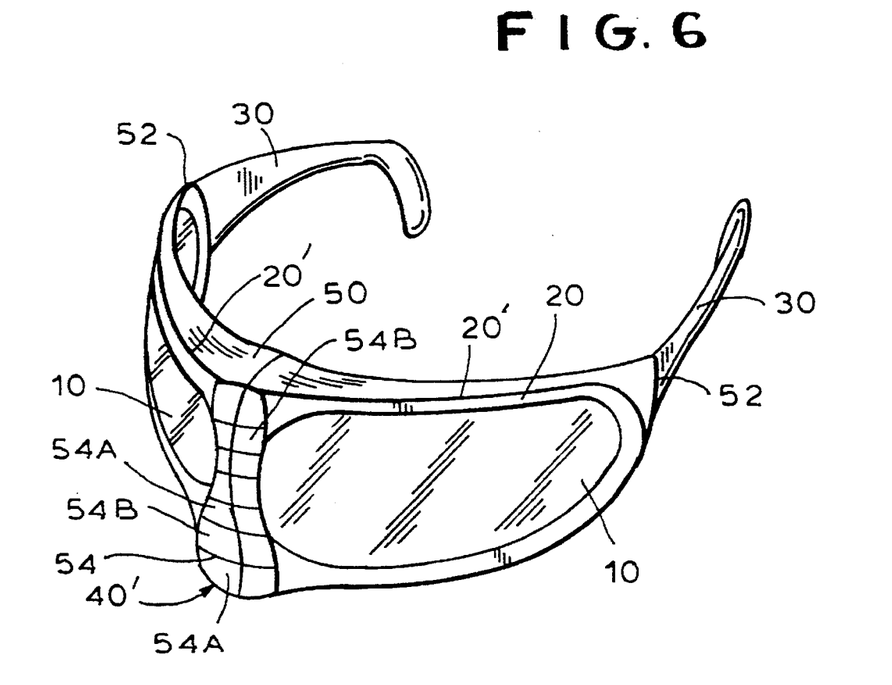
FIG. 6 is a perspective view of a second embodiment of facial wear according to the present invention.
Figure 7:
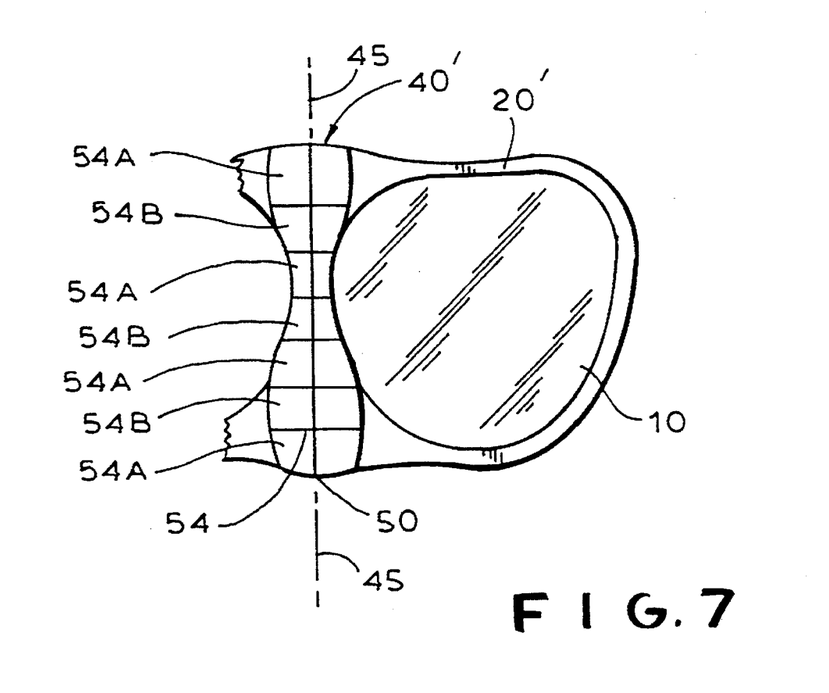
FIG. 7 is a partial front view of facial wear according to FIG. 6.

FIGS. 6–9 show a second embodiment of the present invention. In this embodiment, the lens portions 10 are formed in a wrap around fashion so that they wrap around substantial portions of the sides of the wearer's head. The lens portions 10 are inserted into frame portions 20', which completely enclose each lens 10, as shown in FIG. 6. Temple bars 30 are hingedly coupled at 52 to the respective frame portion 20' as shown in FIG. 6. In addition, frame portions 20' are coupled by a hinge 50 provided at the center of the complete frame 20. Covering the hinge 50 is a fascia 54 which masks the hinge line 50 and serves as a nose protective portion 40' for protecting the nose from the effects of the sun. The fascia 54 of the nose protective portion 40' may have any suitable design, for example, the ridges shown in FIG. 6 and FIG. 7. In the design of FIGS. 6–9, the fascia is comprised of a series of interleaved or interlocked fingers 54A and 54B (FIG. 7). The nose protective portion 40' preferably is shaped so that it provides protection for substantially the wearer's entire nose. Additionally, a suitable nose support may be integrally molded into the frame half portions 20'. Other means of providing nose support, e.g., non-integral piece, may also be employed.

Figure 8:
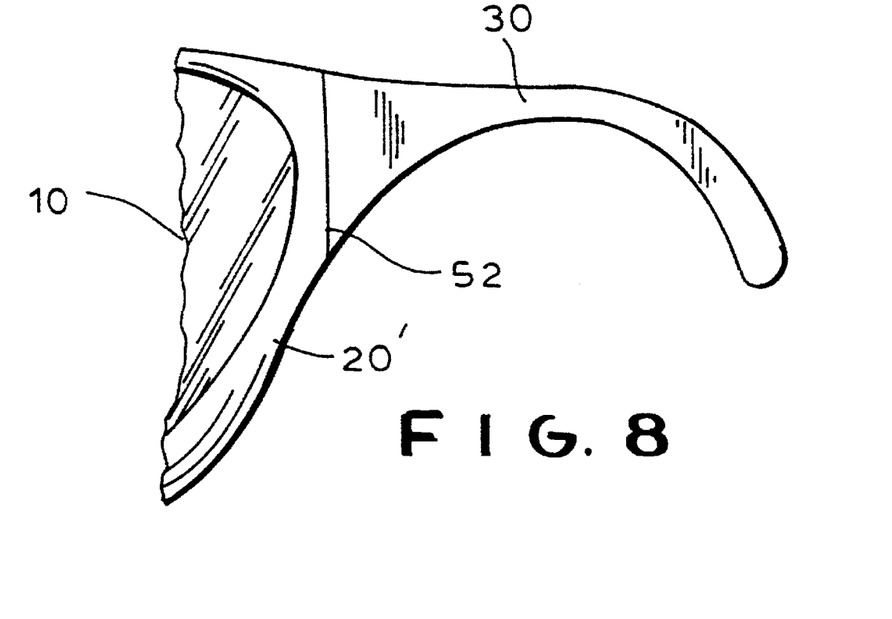
FIG. 8 is a side view of a portion of the facial wear according to FIG. 6.
Figure 9:
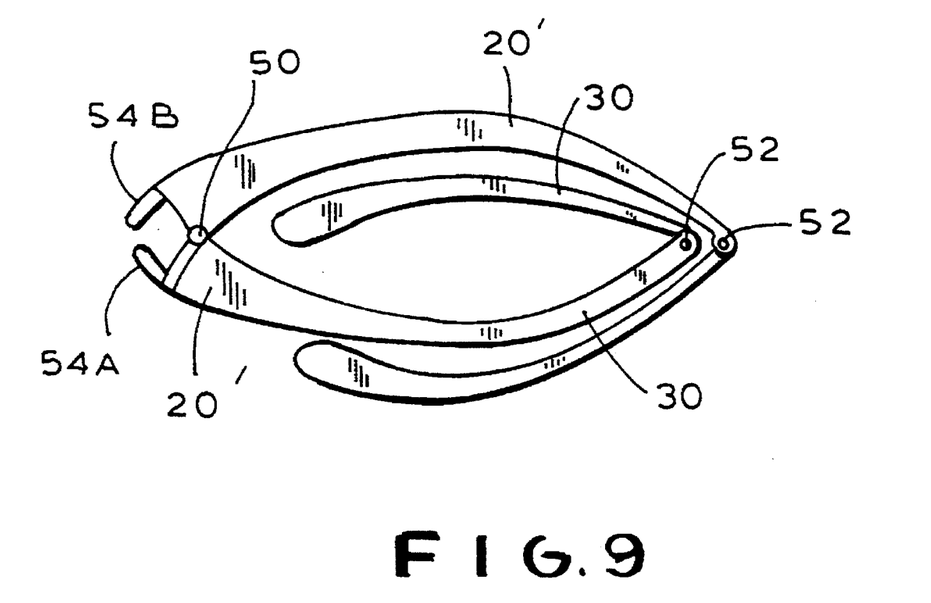
FIG. 9 is a top view of facial wear according to the embodiment of FIG. 6 shown in a folded position.
Figure 10:
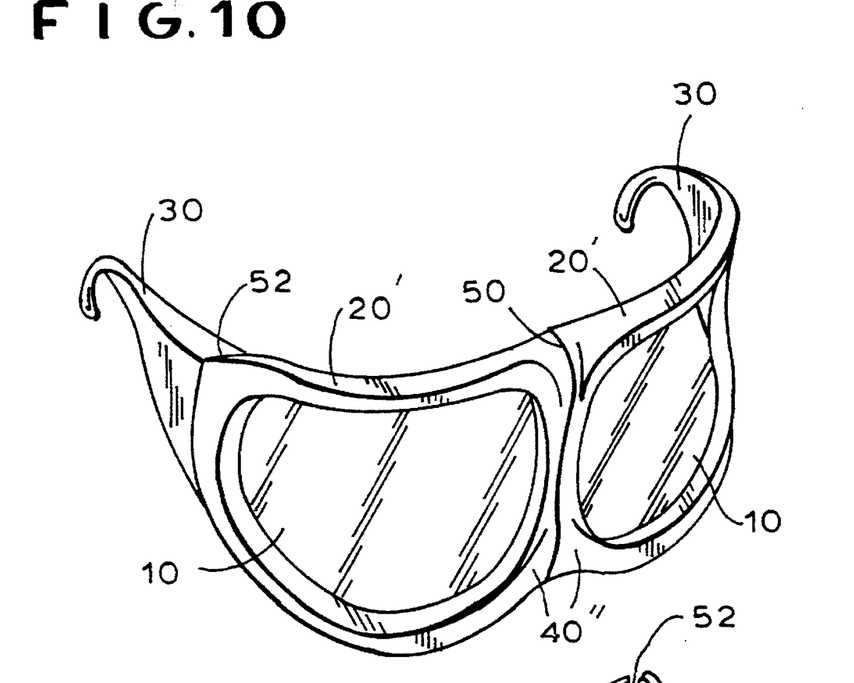
FIG. 10 is a perspective view of a third embodiment of the facial wear according to the present invention.
Figure 11:
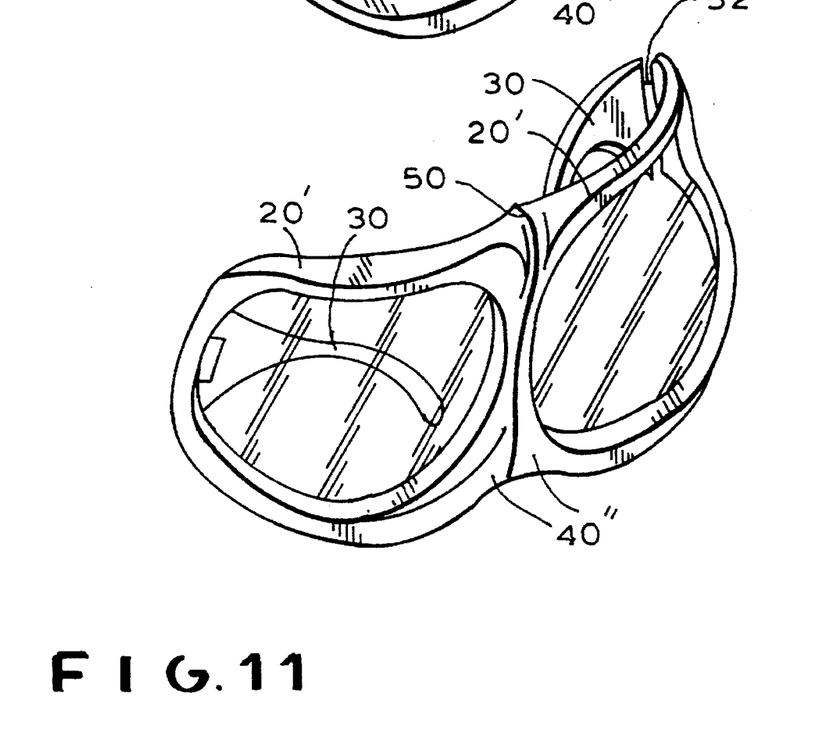
FIG. 11 is a perspective view of the third embodiment according to the present invention shown in a partly folded position.

FIG. 9 shows the facial wear according to the second embodiment of the invention in its completely folded state. As shown, the hinge 50 as well as the hinges 52 where the frame portions 20' and the temples bars 30 are hingedly connected fold as shown. This allows convenient safekeeping of the facial wear when it is not in use. The frame 20 is formed such that one half portion 20' is shorter than the other frame half portion 20' so that the shorter frame half portion 20' and its associated temple bar 30 fold inside or nest in the confines of the other folded frame half portion 20' and its associated temple bar 30. This is shown most clearly in FIG. 9. Preferably, the frame portions and temple bars of the embodiment shown in FIG. 6–9 are made of a suitable plastic material, though other materials can be employed as will be evident to those of skill in the art. Also shown in FIG. 9 is the interleaved nature of the fingers 54A and 54B. As also shown in FIGS. 8 and 9, the temple bars are relatively short due to the wrap around configuration of the lens portions 10 and frame portions 20'.

Figure 12:
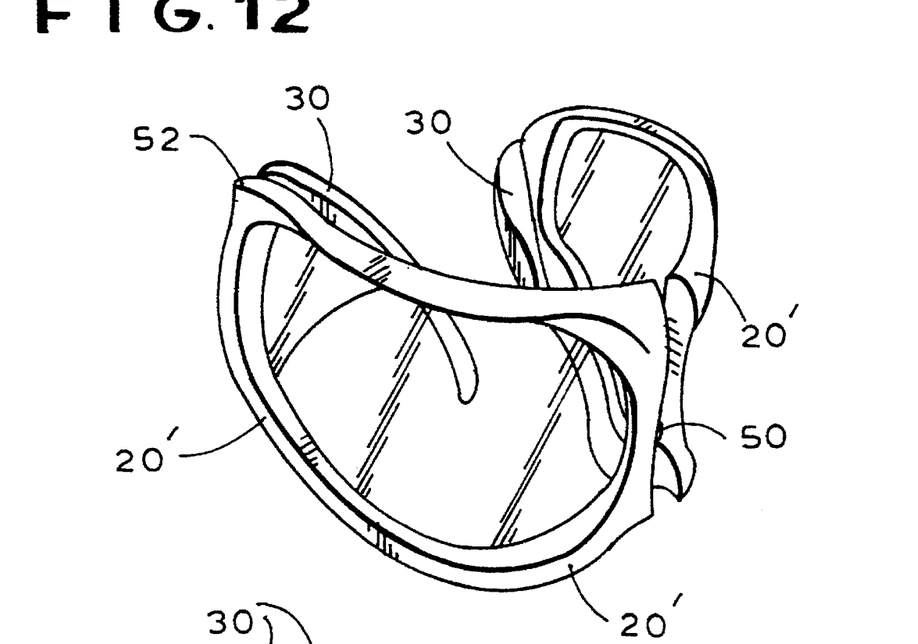
FIG. 12 is a perspective view of the third embodiment shown in a further partially folded view.
Figure 13:
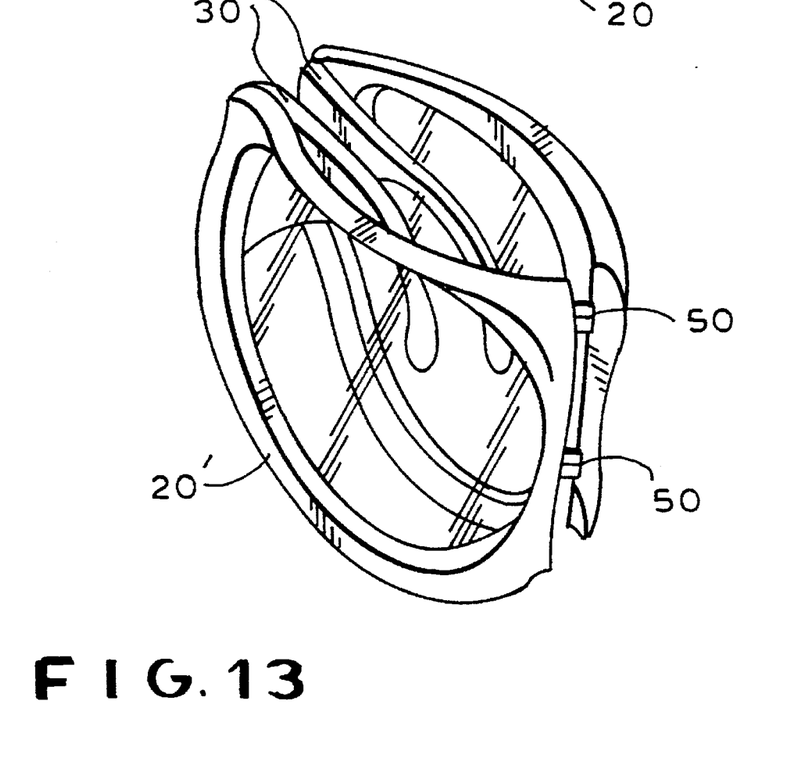
FIG. 13 is a perspective view of the facial wear according to the present invention shown in fully folded position.

FIGS. 10–13 show a third embodiment according to the present invention. In this embodiment, the frame is also divided into half portions 20'. The two half portions are hinged together along a hinge line 50. The temple bars 30 are coupled to the frame half portions 20' at hinge points 52 as in the embodiment shown in FIGS. 6–9. This embodiment also includes wrap around lens portions 10 which wrap around side portions of the wearer's head. In this embodiment, the two frame half portions 20' form a nose protective portion 40" by a thickening of the frame half portions 20' adjacent the hinge line 50. As in the embodiment of FIGS. 6–9, as shown in FIGS. 12 and 13, this embodiment folds along the hinge line 50 as well as at the hinged connection points between the frame portions 20' and the temple bars 30 at 52 to collapse into a small size for storage. However, this embodiment folds without nesting, i.e., the temple bars are adjacent each other in the folded state. See FIG. 13. A suitable nose support is also provided, preferably integrally molded to the frame half portions 20', although other separable type nose supports could also be used, as known to those of skill in the art.

Figures 14, 17:
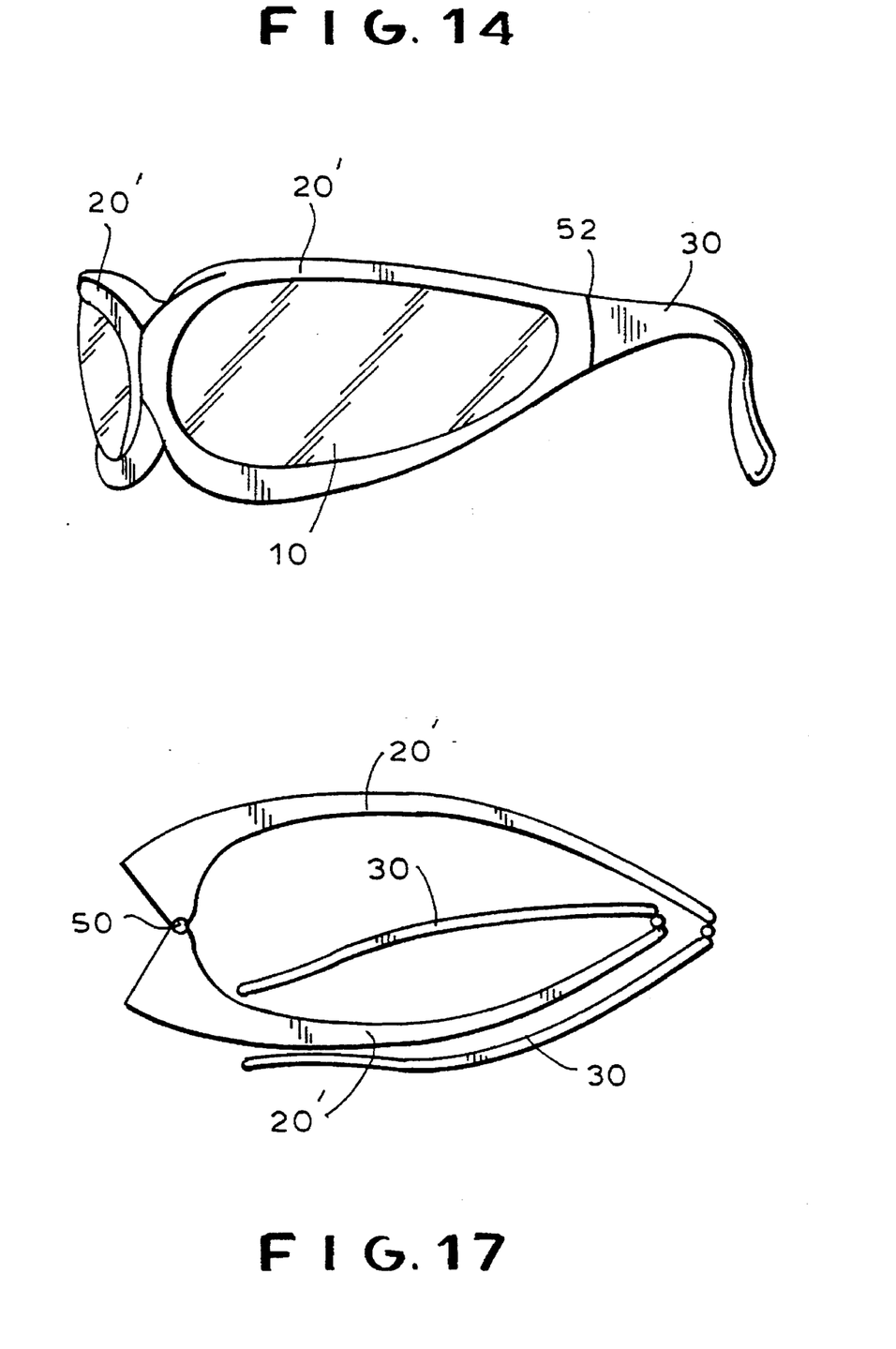
FIG. 14 is a perspective side view of a fourth embodiment according to the present invention.
FIG. 17 is a top view of the facial wear according to the fourth embodiment of the present invention shown in a folded state.
Figure 15:
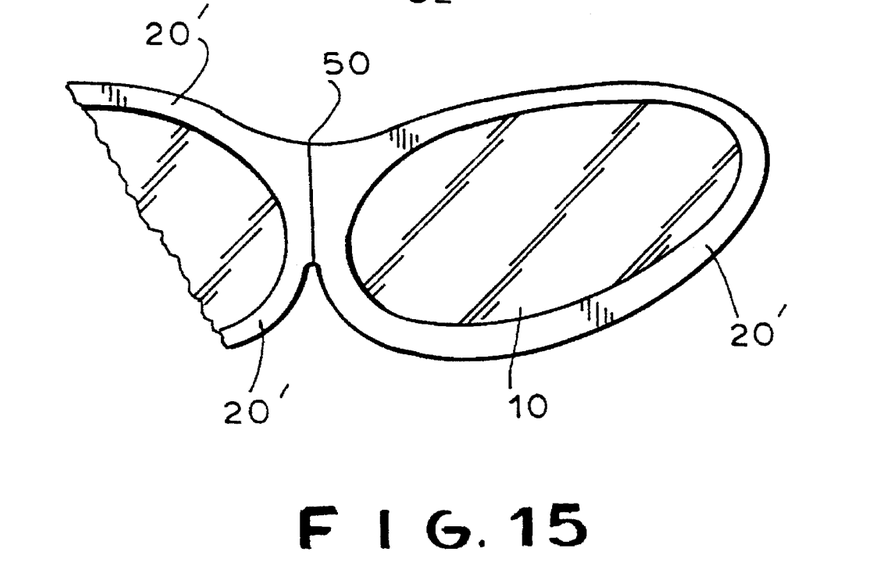
FIG. 15 is a partial front view of the facial wear according to the fourth embodiment.
Figure 16:
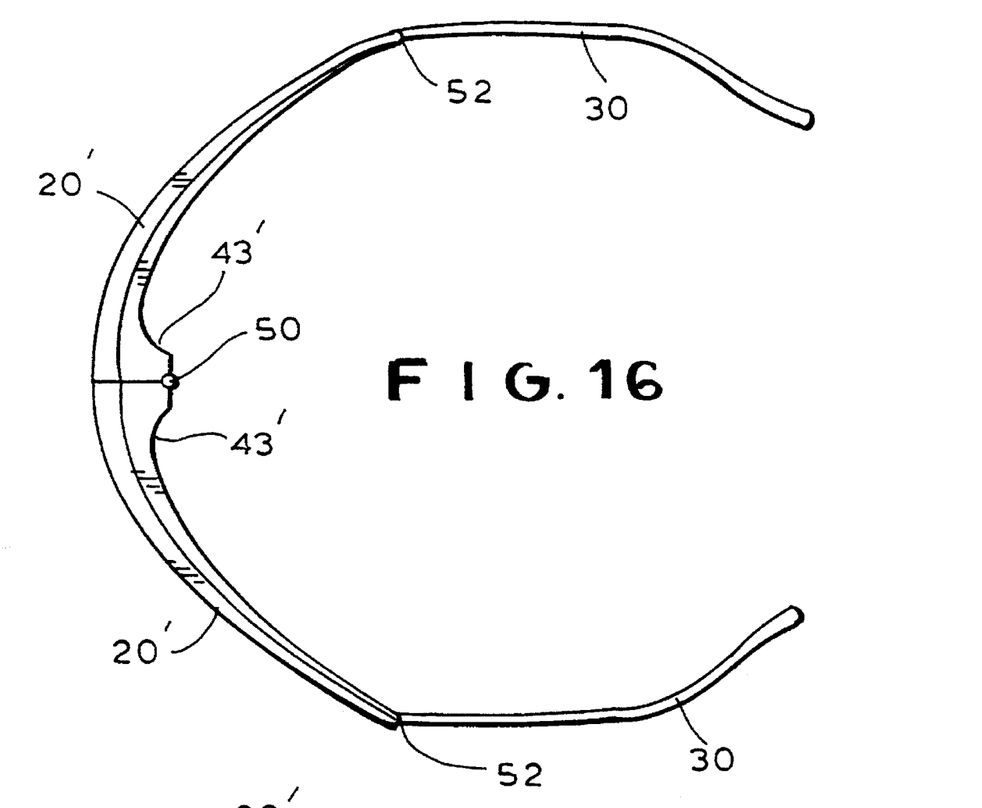
FIG. 16 is a partial top view of the facial wear according to the fourth embodiment of the present invention.

FIG. 14 shows a fourth embodiment of the present invention. This embodiment includes frame half portions 20' which are hingedly coupled to temple bars 30 at 52. Wrap around lens portions 10 are held in the frame portions 20 and wrap a substantial part of the wearer's temple areas. This is illustrated in the top view of FIG. 16 which shows the substantial arc of the two frame half portions 20'. A nose support is integrally molded into each of the frame half portions 20' at 43'. The two frame half portions 20' are hinged along hinge line 50. The temple bars are hingedly coupled to the frame half portions at 52.

As in the second and third embodiments, the fourth embodiment also collapses into a folded state for storage as shown in FIG. 17. The two frame half portions 20' are made such that one is slightly longer than the other, allowing the shorter frame half portion and its associated temple bar 30 to nest within the folded longer frame half portion 20' and its associated temple bar 30.

Figure 18:
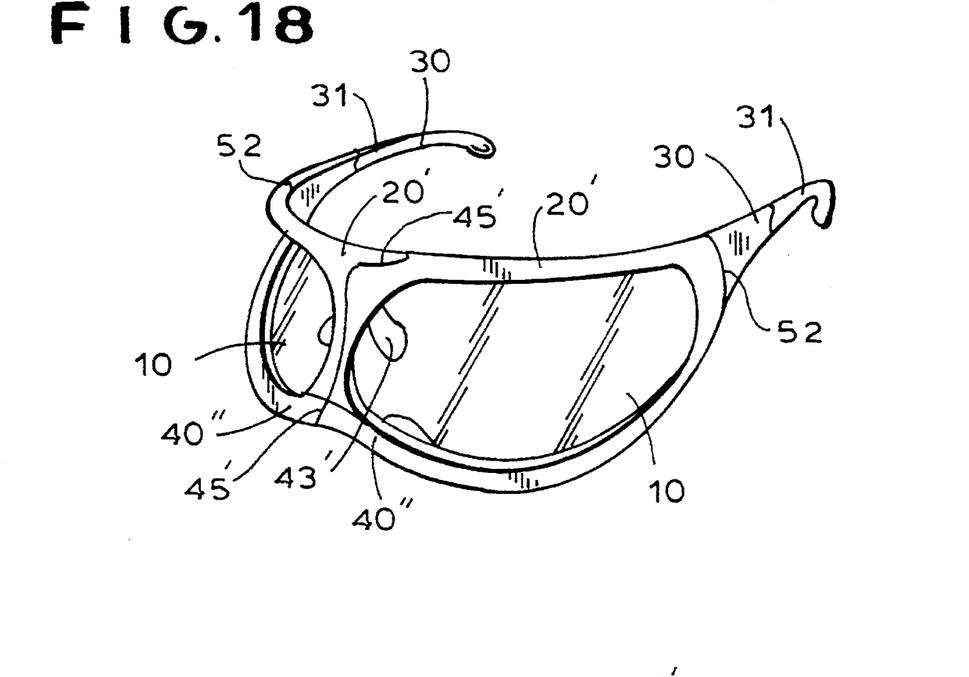
FIG. 18 is a perspective side view of a fifth embodiment of the present invention.
Figure 19:
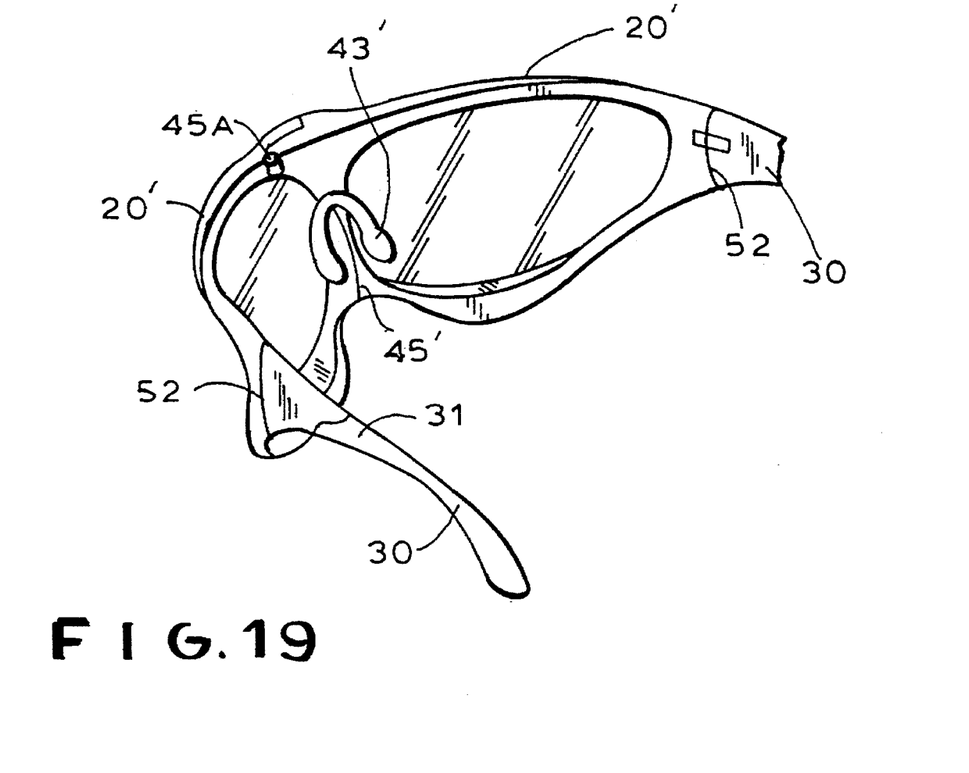
FIG. 19 is a rear perspective view of the fifth embodiment.
Figure 20:
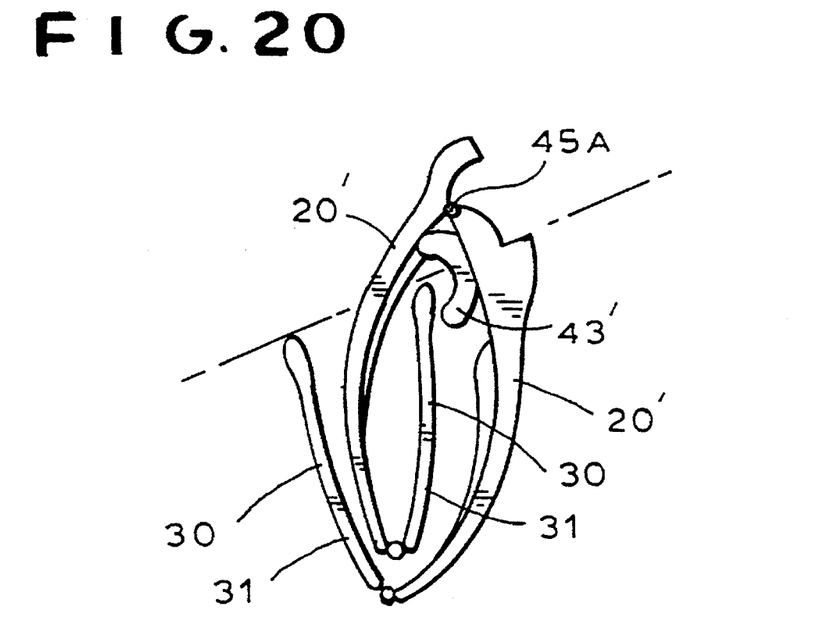
FIG. 20 is a top view showing the fifth embodiment in its folded condition.

FIGS. 18–20 show a fifth embodiment according to the present invention. In the fifth embodiment, the frame 20 is divided into two portions 20' along a joint 45' which is not a straight line. In particular, the joint 45' has an offset so that the hinge 45A is offset towards one of the frame portions 20', in the embodiment shown, the left frame portion 20'. FIG. 20 shows a top view of the facial wear of the fifth embodiment in its completely folded condition, which may have a detent or lock. As shown, the left frame portion 20' and its associated temple bar 30 nest inside the right frame portion 20' and its associated temple bar 30. In addition, a nose support 43' is provided attached to the right frame portion 20'. As shown in FIG. 20, the nose support 43' does not interfere with the folding of the facial wear. Nose rest 43' may be made of a single piece of comfortable plastic material, as known those of skill in the art, and may be attached to the right frame portion 20' by any suitable means, for example, adhesives or other bonding agents. In addition, it may also be made integrally with the frame portion 20' and may take some other appropriate shape.

Figure 21:
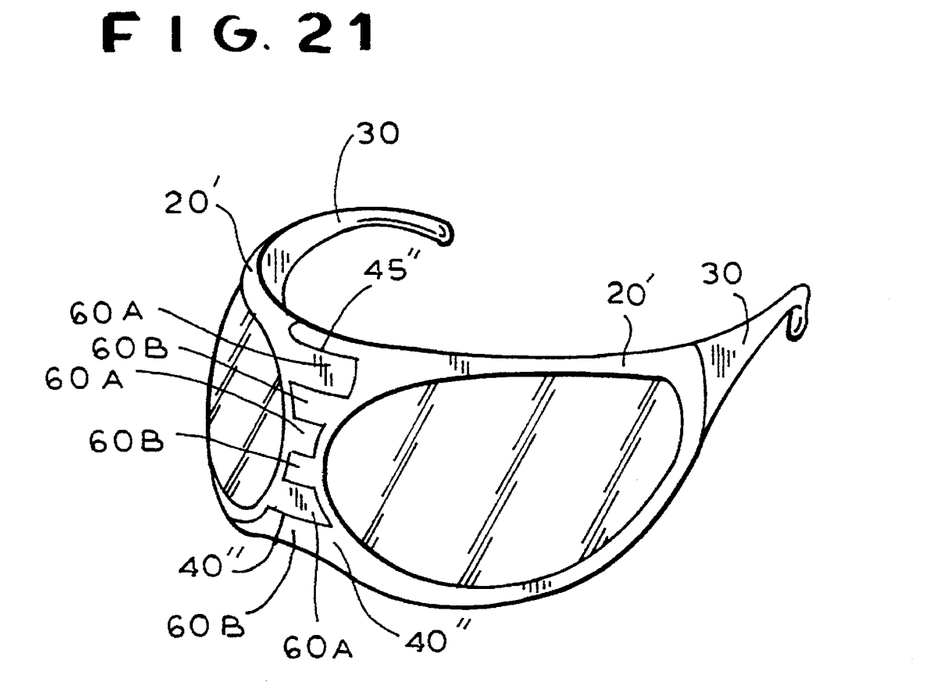
FIG. 21 is a perspective view of a sixth embodiment according to the present invention.
Figure 22:
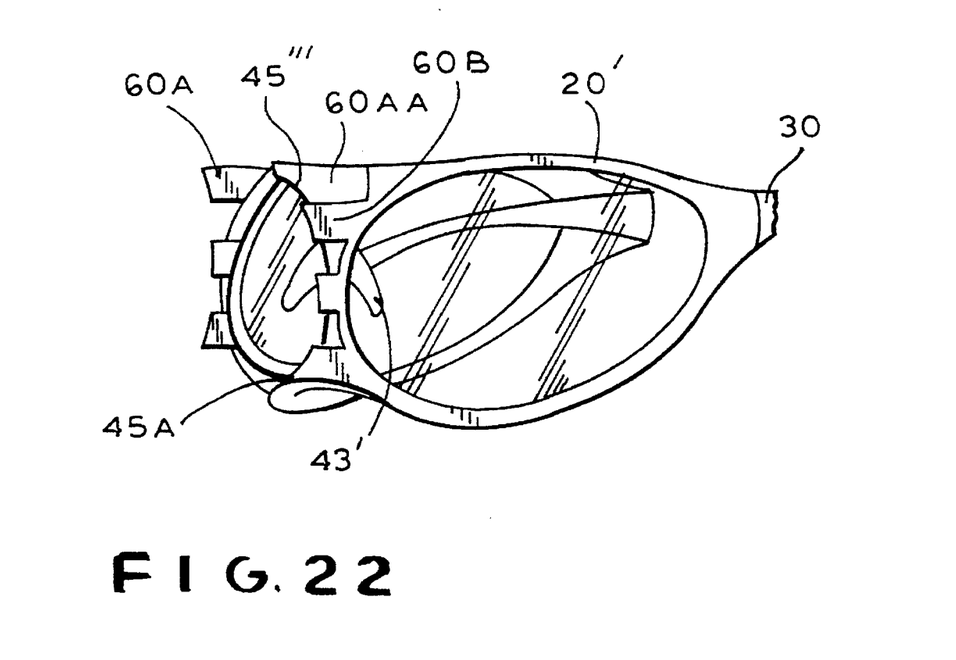
FIG. 22 is a side view of the sixth embodiment showing the facial wear partly folded.
Figure 23:
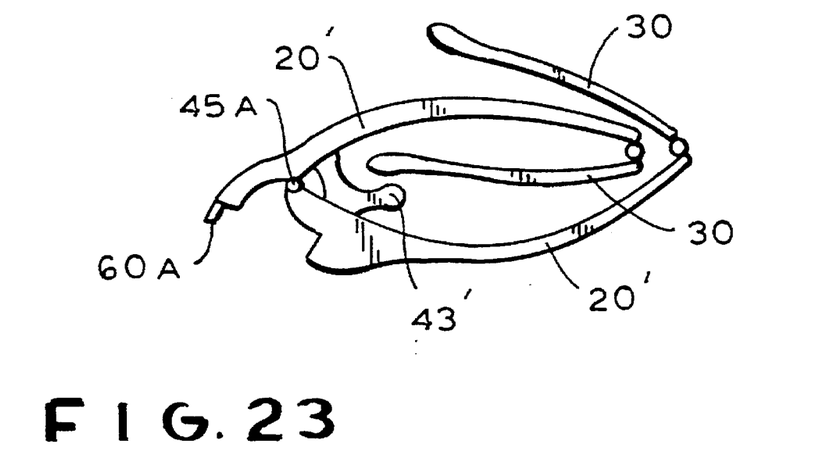
FIG. 23 is a top view showing the sixth embodiment in its folded condition.

FIGS. 21–23 show a sixth embodiment according to the present invention. In this embodiment, the joint line comprises a meandering or interleaved line 45" such that each frame portion 20' has a plurality of interleaved fingers 60A and 60B. This design is somewhat similar to the design of FIGS. 6–9 although there are differences. For example, in the sixth embodiment according to FIGS. 21–23, the joint line 45" is formed such that recesses underlay adjoining fingers of the adjoining frame portion 20'. Thus, as shown in FIG. 22, the finger 60A fits into a recess 60AA in the opposite frame portion 20. Similarly, the finger 60B would fit into a recess, not shown, in the right side frame portion 20'. Additionally, beneath the joining line 45" of the frame portions 20, a curved line 45'" is present where the two frame portions 20' abut, as shown in FIG. 22. As in the embodiment of FIGS. 18–20, a nose support 43' is provided which is attached to one of the frame portions 20', in the illustrated embodiment, the left hand frame portion 20'.

As shown in FIG. 23, the sixth embodiment also folds into the nested form shown there.

In the embodiments of FIGS. 18–20 as well as the other embodiments, the temple bars 30 may be made of a solid plastic, rubber or metal piece or a rubber or soft plastic sheath 31 may be disposed over a portion of a base plastic or metal wire temple bar 30. In this way, the temple bars 30 are adjustable over a wide range to fit a variety of wearers.

In both the embodiment of FIGS. 18–20 and the embodiment of FIGS. 21–23, the nose support 43', as shown, is provided at a location vertically along one of the frame portions 20' so that the facial wear substantially covers not only the wearer's eyes, but also the wearer's nose. As in the other embodiments already described, these embodiments provide a thickening of the frame portions 20' at 40" to assist in protection of the nose of the wearer. However, because of the distance from the face at which the facial wear according to the present invention, when it is worn by the wearer, is disposed on the wearer's face, the lens portions themselves also contribute to the shielding of the wearer's nose from the effects of the sun, particularly from the sides. This is also applicable in the other embodiments described in this specification.

In the embodiment of FIGS. 18–20, the hinge 45A is set recessed into the frame at an offset distance from the center line. The hinge is offset in this way so that the nose support nests easily within the folded facial wear, as shown in FIG. 20.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. Facial protective wear comprising:
   a lens portion for disposition over each eye of a wearer;
   a support frame for attaching each lens portion thereto;
   temple bars coupled hingedly to respective outwardly extending portions of the frame, the temple bars being adapted to provide support on the wearer's ears;
   a nose support disposed between the lens portions for supporting the facial protective wear on the wearer's nose; and
   a nose protective portion disposed between the lenses, the nose protective portion comprising a plurality of horizontally disposed louvers arranged between the lenses.

2. The facial protective wear of claim 1, wherein the louvers are angled downwardly with open areas between the louvers in the shadows of the louvers.

3. The facial protective wear of claim 2, wherein the open areas between louvers provide ventilation for the wearer's face.

4. The facial protective wear of claim 1, wherein the nose support is attached to one of said louvers.

5. The facial protective wear of claim 1, wherein the nose protective portion protects the wearer's nose from the effects of the sun.

6. The facial protective wear of claim 5, wherein the nose protective portion together with the lens portion, protects substantially the wearer's entire nose from the effects of the sun.

7. The facial protective wear of claim 1, wherein the frame is divided into two frame portions, the two frame portions being hinged together to allow the frame to be folded for storage, the two frame portions being hinged together between the two lens portions.

8. The facial protective wear of claim 1, wherein the lens portions protect the wearer's eyes from ultraviolet radiation.

9. Facial protective wear comprising:
   a lens portion for disposition over each eye of a wearer;
   a support frame for attaching each lens portion thereto;
   temple bars coupled hingedly to respective outwardly extending portions of the frame, the temple bars being adapted to provide support on the wearer's ears;
   a nose support disposed between the lens portion for supporting the facial protective wear on the wearer's nose;
   a nose protective portion disposed between the lens portions;
   the frame being divided into two frame portions, the two frame portions each supporting a respective lens portion, the two frame portions being coupled together with a hinge between the two lens portions at the nose protective portion so that the facial protective wear can be folded into a collapsed state for storage;
   and further wherein the nose protective portion protects substantially the wearer's entire nose from the effects of the sun.

10. The facial protective wear of claim 9, wherein a front face of the hinge is hidden from view by a fascia of the nose protective portion.

11. The facial protective wear of claim 10, wherein the fascia comprises a plurality of interlocked fingers, at least one attached to one frame portion and the other to the other frame portion.

12. The facial protective wear of claim 9, wherein the lens portions each wrap around a portion of a side of the wearer's head.

13. The facial protective wear of claim 9, wherein the lens portions protect the wearer's eyes from ultraviolet radiation.

14. The facial protective wear of claim 9, wherein the temple bars are arranged side by side when the facial protective wear is collapsed for storage.

15. The facial protective wear of claim 9 wherein the lens portions provide protection, at least in part, for the wearer's nose.

16. The facial protective wear of claim 15 wherein the lens portions provide protection for the wearer's nose from directions on either side of the wearer.

17. The facial protective wear of claim 9, wherein the nose support is attached to one of said frame portions.

18. The facial protective wear of claim 9 wherein the hinge is disposed offset from a vertical center line of the frame.

19. The facial protective wear of claim 9, wherein one of the frame portions and its associated temple bar nest within the other frame portion and its associated temple bar when the facial protective wear is collapsed for storage.

20. The facial protective wear of claim 9, wherein the temple bars are enlarged at their attachment points to the support frame to provide additional protection from the sun to side areas of the wearer's head.

21. Facial protective wear comprising:
   a lens portion for disposition over each eye of a wearer;
   a support frame for attaching each lens portion thereto;
   temple bars coupled hingedly to respective outwardly extending portions of the frame, the temple bars being adapted to provide support on the wearer's ears;
   a nose support disposed between the lens portion for supporting the facial protective wear on the wearer's nose;
   a nose protective portion disposed between the lens portions;

the frame being divided into two frame portions, the two frame portions each supporting a respective lens portion, the two frame portions being coupled together with a hinge between the two lens portions at the nose protective portion so that the facial protective wear can be folded into a collapsed state for storage;

and further wherein one frame portion is smaller in length than the other frame portion, the smaller frame portion and its associated temple bar nesting within the longer frame portion and its associated temple bar when the facial protective wear is collapsed for storage.

22. Facial protective wear comprising:

a lens portion for disposition over each eye of a wearer;

a support frame for attaching each lens portion thereto;

temple bars coupled hingedly to respective outwardly extending portions of the frame, the temple bars being adapted to provide support on the wearer's ears;

a nose support disposed between the lens portion for supporting the facial protective wear on the wearer's nose;

a nose protective portion disposed between the lens portions;

the frame being divided into two frame portions, the two frame portions each supporting a respective lens portion, the two frame portions being coupled together with a hinge between the two lens portions at the nose protective portion so that the facial protective wear can be folded into a collapsed state for storage;

and further wherein the nose protective portion comprises a thickening of lower adjoining sections of the two frame portions where the frame portions overly a wearer's nose;

said nose protective portion substantially protecting the wearer's entire nose from the effects of the sun.

23. Facial protective wear comprising:

a lens portion for disposition over each eye of a wearer;

a support frame for attaching each lens portion thereto;

temple bars coupled hingedly to respective outwardly extending portions of the frame, the temple bars being adapted to provide support on the wearer's ears;

a nose support disposed between the lens portion for supporting the facial protective wear on the wearer's nose;

a nose protective portion disposed between the lens portions;

the frame being divided into two frame portions, the two frame portions each supporting a respective lens portion, the two frame portions being coupled together with a hinge between the two lens portions at the nose protective portion so that the facial protective wear can be folded into a collapsed state for storage;

and further wherein the frame portions define a meandering line between the frame portions at the nose protective portion, the meandering line being formed by a plurality of fingers disposed on opposite ones of said frame portions that interleave when said frame portions abut when said facial protective wear is in use.

24. Facial protective wear comprising:

a lens portion for disposition over each eye of a wearer;

a support frame for attaching each lens portion thereto;

temple bars coupled hingedly to respective outwardly extending portions of the frame, the temple bars being adapted to provide support on the wearer's ears;

a nose support disposed between the lens portions for supporting the facial protective wear on the wearer's nose; and the frame being divided into two frame portions, the two frame portions being hingedly coupled together at a location between the two lens portions, the two frame portions being of unequal length, one frame portion being longer than the other frame portion comprising a shorter frame portion, the shorter frame portion and its associated temple bar nesting in the longer frame portion and its associated temple bar when the facial protective wear is collapsed for storage.

25. The facial protective wear of claim 24, wherein the lens portions each wrap around a portion of a side of the wearer's head.

26. The facial protective wear of claim 24, wherein the lens portions protect the wearer's eyes from ultraviolet radiation.

27. The facial protective wear of claim 24, wherein the temple bars are enlarged at their attachment points to the support frame to provide additional protection from the sun to side areas of the wearer's head.

28. Facial protective wear comprising a lens portion for disposition over each eye of a wearer;

a support frame for attaching each lens portion thereto, the support frame having a central portion between the lens portions;

temple bars coupled hingedly to respective outwardly extending portions of the frame, the temple bars being adapted to provide support on the wearer's ears;

a nose support disposed between the lens portions for supporting the facial protective wear on the wearer's nose; and a nose protective portion disposed between the lenses, the nose protective portion comprising a part of the central portion of the support frame;

and further wherein the nose protective portion, together with the lens portion, protects substantially the wearer's entire nose from the effects of the sun.

29. The facial protective wear of claim 28, wherein the frame is divided into two frame portions, the two frame portions being hinged together to allow the frame to be folded for storage, the two frame portions being hinged together between the two lens portions.

30. The facial protective wear of claim 29, wherein one of said frame portions and its associated temple bar nest within the other frame portion and its associated temple bar when the facial protective wear is collapsed for storage.

31. The facial protective wear of claim 28, wherein the lens portions protect the wearer's eyes from ultraviolet radiation.

32. The facial protective wear of claim 28, wherein the temple bars are enlarged at their attachment points to the support frame, thereby providing additional protection from the sun to side areas of the wearer's head.

33. The facial protective wear of claim 28, wherein the nose protective portions is an integral part of the central portion of the support frame.

34. Facial protective wear comprising:

a lens portion for disposition over each eye of a wearer;

a support frame for attaching each lens portion thereto;

temple bars coupled hingedly to respective outwardly extending portions of the frame, the temple bars being adapted to provide support on the wearer's ears;

a nose support disposed between the lens portions for supporting the facial protective wear on the wearer's nose;

the frame being divided into two framed portions, the two frame portions being hingedly coupled together at a location between the two lens portions, the two frame portions being such that one frame portion and its associated temple bar nest in the other frame portion and its associated temple bar when the facial protective wear is collapsed for storage;

a nose protective portion disposed between the lens portions, the nose protective portion protecting substantially the wearer's entire nose from the effects of the sun.

35. Facial protective wear comprising:

a lens portion for disposition over each eye of a wearer;

a support frame for attaching each lens portion thereto;

temple bars coupled hingedly to respective outwardly extending portions of the frame, the temple bars being adapted to provide support on the wearer's ears;

a nose support disposed between the lens portion for supporting the facial protective wear on the wearer's nose;

a nose protective portion disposed between the lens portions;

the frame being divided into two frame portions, the two frame portions each supporting a respective lens portion, the two frame portions being coupled together with a hinge between the two lens portions at the nose protective portion so that the facial protective wear can be folded into a collapsed state for storage;

and further wherein one frame portion is smaller in length than the other frame portion, the smaller frame portion and its associated temple bar nesting within the longer frame portion and its associated temple bar when the facial protective wear is collapsed for storage.

36. Facial protective wear comprising:

a lens portion for disposition over each eye of a wearer;

a support frame for attaching each lens portion thereto;

temple bars coupled hingedly to respective outwardly extending portions of the frame, the temple bars being adapted to provide support on the wearer's ears;

a nose support disposed between the lens portions for supporting the facial protective wear on the wearer's nose;

a nose protective portion disposed between the lens portions;

the frame being divided into two frame portions, the two frame portions each supporting a respective lens portion, the two frame portions being coupled together with a hinge between the two lens portions at the nose protective portion so that the facial protective wear can be folded into a collapsed state for storage;

each one of a hinge between a temple bar and a respective one of the frame portions to which the temple bar is hingedly connected being located at a different distance from the hinge between the two lens portions such that one of the frame portions and its associated temple bar can nest within the other of the frame portions and its associated temple bar when the facial protective wear is collapsed for storage.

37. Facial protective wear comprising:

a lens portion for disposition over each eye of the wearer;

a support frame for attaching each lens portion thereto;

temple bars coupled hingedly to respective outwardly extending portions of the frame, the temple bars being adapted to provide support on the wearer's ears;

a nose support disposed between the lens portions for supporting the facial protective wear on the wearer's nose;

the frame being divided into two frame portions, the two frame portions being hingedly coupled together at a location between the two lens portions;

each one of a hinge between a temple bar and a respective one of the frame portions to which the temple bar is hingedly connected being located at a different distance from the hinge between the two lens portions such that one of the frame portions and its associated temple bar can nest within the other of the frame portions and its associated temple bar when the facial protective wear is collapsed for storage.

38. Facial protective wear comprising:

a lens portion for disposition over each eye of the wearer;

a support frame for attaching each lens portion thereto;

temple bars coupled hingedly to respective outwardly extending portions of the frame, the temple bars being adapted to provide support on the wearer's ears;

a nose support disposed between the lens portions for supporting the facial protective wear on the wearer's nose;

the frame being divided into two frame portions, the two frame portions being hingedly coupled together by a hinge at a location between the two lens portions;

the hinge being disposed off center from a center line disposed vertically between the two frame portions allowing one of the frame portions and its associated temple bar to nest in the other frame portion and its associated temple bar when the facial protective wear is collapsed for storage.

* * * * *